United States Patent
Küsters et al.

(10) Patent No.: US 9,415,024 B2
(45) Date of Patent: Aug. 16, 2016

(54) AMINOALKANOL DERIVATIVES

(71) Applicants: Ernst Küsters, Eschbach (DE); Lukas Oberer, Tenniken (CH); Gottfried Sedelmeier, Schallstadt (DE)

(72) Inventors: Ernst Küsters, Eschbach (DE); Lukas Oberer, Tenniken (CH); Gottfried Sedelmeier, Schallstadt (DE)

(73) Assignee: Novartis AG, Basel (CH)

( * ) Notice: Subject to any disclaimer, the term of this patent is extended or adjusted under 35 U.S.C. 154(b) by 391 days.

(21) Appl. No.: 13/917,600

(22) Filed: Jun. 13, 2013

(65) Prior Publication Data

US 2013/0289127 A1 Oct. 31, 2013

Related U.S. Application Data

(63) Continuation of application No. 10/575,827, filed as application No. PCT/EP2004/011567 on Oct. 14, 2004, now abandoned.

(30) Foreign Application Priority Data

Oct. 15, 2003 (GB) .................................. 0324210.4

(51) Int. Cl.
| | |
|---|---|
| C07C 215/28 | (2006.01) |
| C07C 233/22 | (2006.01) |
| A61K 31/137 | (2006.01) |
| A61K 31/135 | (2006.01) |
| A61K 45/06 | (2006.01) |

(52) U.S. Cl.
CPC ............. A61K 31/137 (2013.01); A61K 31/135 (2013.01); A61K 45/06 (2013.01); C07C 215/28 (2013.01); C07C 233/22 (2013.01)

(58) Field of Classification Search
CPC .. A61K 31/135; A61K 31/137; C07C 215/28; C07C 233/22
See application file for complete search history.

(56) References Cited

U.S. PATENT DOCUMENTS

| | | | |
|---|---|---|---|
| 5,604,229 | A | 2/1997 | Fujita et al. |
| 6,004,565 | A | 12/1999 | Chiba et al. |
| 7,001,494 | B2 | 2/2006 | Jovic et al. |
| 2007/0010494 | A1 | 1/2007 | Ehrhardt |

FOREIGN PATENT DOCUMENTS

| | | |
|---|---|---|
| EP | 0627406 A1 | 12/1994 |
| EP | 0812588 A1 | 12/1997 |
| EP | 1002792 A1 | 5/2000 |
| EP | 1319651 A2 | 6/2003 |
| EP | 1431275 A1 | 6/2004 |
| EP | 1431284 A1 | 6/2004 |
| JP | 10147587 A2 | 6/1998 |
| JP | 2004/307439 A2 | 11/2004 |
| JP | 2004/307440 A2 | 11/2004 |

OTHER PUBLICATIONS

Brinkmann Volker et al. J.o.Biol.Chem. Baltimore, USA, vol. 227, No. 24, pp. 21453 – 21457.

*Primary Examiner* — Kortney L Klinkel
(74) *Attorney, Agent, or Firm* — Andrew Holmes

(57) ABSTRACT

Disclosed are compounds of formula I

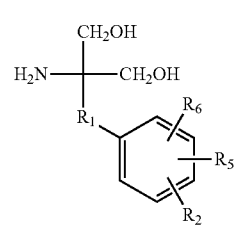

wherein $R_1$, $R_2$, $R_5$ and $R_6$ are as defined in the claims; such compounds have interesting pharmacological properties.

2 Claims, No Drawings

AMINOALKANOL DERIVATIVES

The present invention relates to aminoalkanol derivatives and their use as pharmaceuticals, a process for preparing such compounds and to intermediate compounds useful in such a process.

More particularly, the invention relates to a compound of formula I

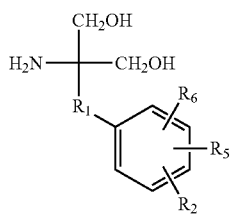

wherein
$R_1$ is $C_{2-8}$-alkylene;
$R_2$ is $C_{1-20}$-alkyl, optionally substituted by halogen;
$R_5$ is H or $C_{1-20}$-alkyl; and
$R_6$ is $C_{1-20}$alkyl or a radical of formula a)

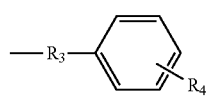

wherein $R_3$ is $C_{2-8}$-alkylene and $R_4$ is H or $C_{1-20}$alkyl, optionally substituted by halogen, in free or salt form.

Alkyl means straight or branched alkyl.

In one embodiment of the invention, $R_6$ is $C_{1-20}$alkyl. In another embodiment, $R_6$ is a radical of formula a). When $R_5$ or $R_6$ is $C_{1-20}$alkyl, it may preferably be alkyl with up to 14 carbon atoms.

Preferred compounds of formula I are those wherein $R_1$ and/or $R_3$ in the radical of formula a) is $C_{1-4}$alkylene, e.g. ethylene. The radical of formula a) may be in ortho, meta or para, preferably in meta or ortho.

$R_2$ is preferably $C_{6-14}$-alkyl, e.g. octyl, optionally substituted by halogen. $R_2$ may be in ortho, meta or para, preferably in para.

$R_6$ is preferably a radical of formula a). $R_4$ is preferably H or $C_{6-14}$-alkyl, e.g. octyl, optionally substituted by halogen. $R_4$ may be in ortho, meta or para, preferably in para.

Particularly preferred compounds are those of formula II

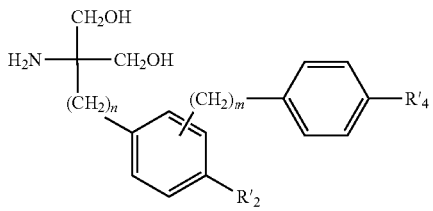

wherein
n is an integer from 1 to 4, e.g. 2;
m is an integer from 2 to 4, e.g. 2;
$R'_2$ is $C_{6-14}$-alkyl, e.g. octyl; and
$R'_4$ is H or $C_{6-14}$-alkyl, e.g. H or octyl;
in free or salt form.

The compounds of the invention may exist in free form or in salt form, e.g. addition salts with e.g. organic or inorganic acids, for example trifluoroacetic acid or hydrochloride acid.

Compounds of formula I and salts of the present invention encompass hydrate and solvate forms.

A compound of formula I may be prepared by deprotecting a compound of formula III:

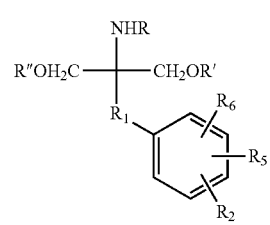

wherein $R_1$, $R_2$, $R_5$ and $R_6$ are as defined in formula I, and each of R, R' and R" is a protecting group; and recovering the resulting compound of formula I in free or salt form.

The process may be performed according to methods known in the art, for example by base- or acid-catalysed hydrolysis, e.g. as described in the examples.

Protecting groups, their introduction and removal are described, for example, in "Protective Groups in Organic Synthesis", T. W. Greene et al., John Wiley & Sons Inc., Second Edition 1991. Preferably each protecting group, e.g. the amino protecting group R and/or one or both of the hydroxy protecting groups R' and R", is acyl, e.g. a residue $R_y$—CO— wherein $R_y$ is $C_{1-6}$alkyl, $C_{3-6}$cycloalkyl, phenyl or phenyl-$C_{1-4}$alkyl, e.g. acetyl.

Where required, the compound of formula I obtained in free form may be converted into the desired salt form, or vice versa.

A compound of formula III used as starting material and wherein $R_6$ is a radical of formula a) may be prepared by reducing a compound of formula IV

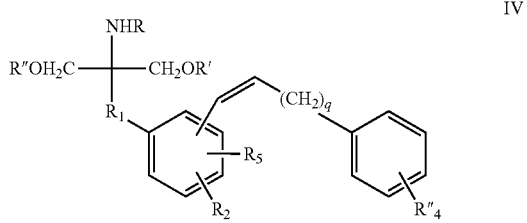

wherein
R, R', R", $R_1$, $R_2$ and $R_5$ are as defined above;
$R''_4$ either has the meaning of $R_4$ or is —CO—$C_{1-19}$alkyl; and
q is an integer from 0 to 6;
using known methods, e.g. reduction with hydrogen and a palladium catalyst. The compound of formula IV may be in the cis or trans form.

A compound of formula IV may be prepared by reacting a compound of formula V

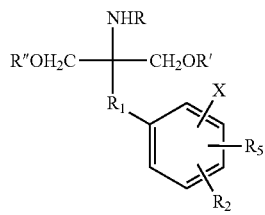

wherein R, R', R", $R_1$, $R_2$ and $R_5$ are as defined above; and X is halogeno, e.g. bromo;
with a compound of formula VI:

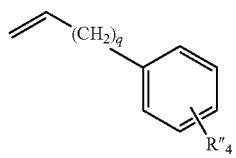

wherein q and $R''_4$ are as defined above;
e.g. using known methods, for example by Heck coupling, e.g. reaction with $Pd(P(C_6H_5)_3)_4$ or $Pd(II)$-acetate/$P(t$-$Bu)_3$.

Preferred compounds of formulae V and VI are those which may be used to produce a compound of formula II, i.e. compounds of formula V wherein $R_1$ is $C_{1-4}$alkylene and $R_2$ is in the position para and is equal to $R'_2$ as defined in formula II, and compounds of formula VI wherein $R_4$ is in the position para and is equal to $R'_4$ as defined in formula II, the radical of formula (a) being preferably in position meta or ortho.

A compound of formula V may be prepared by halogenating, e.g. brominating with a brominating agent, e.g. HBr, $Br_2$ or N-bromosuccinimide, a compound of formula VII:

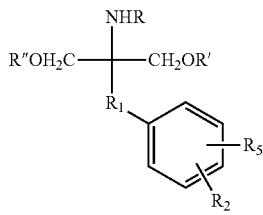

wherein R, R', R", $R_1$, $R_2$ and $R_5$ are as defined above. Isomers of compounds of formula V formed by this process, in which the halogen atom is attached to the benzene ring at alternative positions, may be separated by standard procedures, e.g. column chromatography. Preferably the bromination with N-bromosuccinimide is carried out at room temperature.

The compounds of formulae III to V are intermediates useful in the production of the compounds of formulae I and II and also form part of the present invention. The compounds formulae VI and VII are known or may be produced in accordance with known procedures.

The following non-limiting examples illustrate the invention.

EXAMPLE

2-Amino-2-(2-{4-octyl-3-[2-(4-octyl-phenyl)-ethyl]-phenyl}-ethyl)-propane-1,3-diol (1) and 2-Amino-2-(2-{4-octyl-2-[2-(4-octyl-phenyl)-ethyl]-phenyl}-ethyl)-propane-1,3-diol (2)

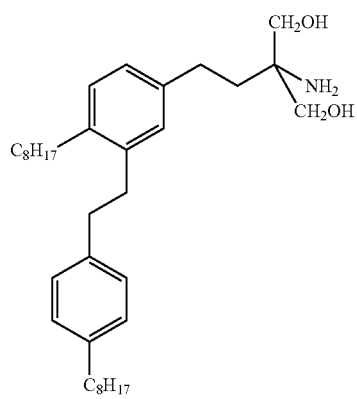

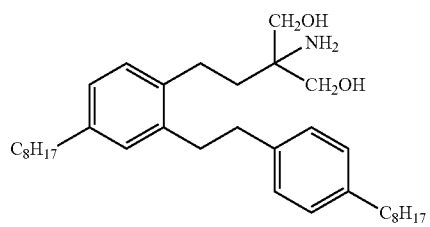

a) 400 ml acetic acid are added to 30 g acetic acid 2-acetoxymethyl-2-acetylamino-4-(4-octyl-phenyl)-butyl ester. To this colorless solution are added at room temperature 24.6 g N-bromosuccinimide and the resulting mixture is stirred at room temperature and in the darkness for one month. Thereafter 1 l methylene chloride is added and the mixture is washed with water. The organic phase is evaporated to dryness, yielding a brown crystalline residue comprising a mixture of 2 bromo-isomers wherein Br is in ortho or in para:

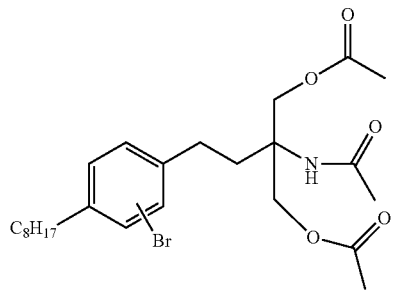

The resulting 2 isomers are separated by column chromatography on chiralpak-AD using a mixture of 100:5 V/V of n-hexane/propanol as eluent.

b1) 6 g acetic acid 2-acetoxymethyl-2-acetylamino-4-(3-bromo-4-octyl-phenyl)-butyl ester, 0.87 g sodium acetate, 3.08 g 4-octanoyl-1-vinyl-benzene and 2.06 g tetrakis-(triphenylphosphine)-Pd are dissolved in 120 ml dimethylformamide and the mixture is heated to 150° C. for 2 hours. A further 0.52 g tetrakis-(triphenylphosphine)-Pd is added and the mixture is further heated at 150° C. for 2 hours. The black mixture is concentrated to dryness. 10 ml acetonitrile are added, the mixture is filtered on Cellflok and concentrated again. The resulting brown oil is dissolved with 50 ml acetonitrile and purified by column chromatography eluting with acetonitrile, yielding acetic acid 2-acetoxymethyl-2-acetylamino-4-{4-octyl-2-[3-(4-octyl-phenyl)-vinyl]-phenyl}-butyl ester.

b2) 22.5 g acetic acid 2-acetoxymethyl-2-acetylamino-4-(2-bromo-4-octyl-phenyl)-butyl ester, 1.21 g sodium acetate, 4.25 g 4-octanoyl-1-vinyl-benzene and 277 mg Pd acetate are dissolved in 200 ml dimethylformamide and the mixture is heated to 150° C. After addition of 1.2 ml tri-t.-butyl-phosphine, the mixture is stirred for 2 hours at 150° C. When the reaction is completed, 5 ml water are added. The black residue is concentrated to dryness and treated as disclosed above b1). Acetic acid 2-acetoxymethyl-2-acetylamino-4-{4-octyl-2-[2-(4-octyl-phenyl)-vinyl]-phenyl}-butyl ester is purified by column chromatography using acetonitrile as eluent.

c1) 2.01 g of the compound of b1) are dissolved in 200 ml ethanol, 5×400 mg Pd/C are added and the mixture is hydrogenated with $H_2$ until complete. The mixture is then filtered and concentrated to dryness.

c2) 2.28 g of the compound of b2) are dissolved in 200 ml ethanol, 4×285 mg Pd/C are added and the mixture is hydrogenated with $H_2$ until complete. The mixture is then filtered and concentrated to dryness.

d1) 1.68 g of the compound of c2) is dissolved in 15 ml methanol and heated to 50° C. There is added a mixture of 4.25 ml water and 1.0 ml NaOH. The resulting mixture is stirred for 2 hours at 70° C. The mixture is extracted with 3.1 l methylene chloride and 2.1 l water, dried with magnesium sulfate and evaporated to dryness, yielding the title compound 1 which is purified by column chromatography using hexane/isopropanol 70/30 as eluent.

d2) 2.35 g of the compound of c1) is dissolved in 20 ml methanol and heated to 50° C. There is added a mixture of 6 ml water and 1.46 ml NaOH. The resulting mixture is stirred for 2 hours at 70° C. The mixture is extracted with 3.1 l methylene chloride and 2.1 l water, dried with magnesium sulfate and evaporated to dryness, yielding the title compound 2 which is purified by column chromatography using hexane/ethanol (70/30→80/20) as eluent.

The NMR data are in line with the 2 title compounds.

The compounds of formula I, in free form or in pharmaceutically acceptable salt form, exhibit valuable pharmacological properties, e.g. agonism of S1P receptors, e.g. as indicated in in vitro and in vivo tests and are therefore indicated for therapy.

A. Binding Affinity of SIP Receptor Agonists to Individual Human SIP Receptors

Transient Transfection of Human S1P Receptors into HEK293 Cells

S1P receptors and $G_i$ proteins are cloned, and equal amounts of 4 cDNAs for the EDG receptor, $G_i$-α, $G_i$-β and $G_i$-γ are mixed and used to transfect monolayers of HEK293 cells using the calcium phosphate precipitate method (M. Wigler et al., Cell. 1977; 11; 223 and DS. Im et al., Mol. Pharmacol. 2000; 57; 753). Briefly, a DNA mixture containing 25 μg of DNA and 0.25 M CaCl is added to HEPES-buffered 2 mM $Na_2HPO_4$. Subconfluent monolayers of HEK293 cells are poisoned with 25 mM chloroquine, and the DNA precipitate is then applied to the cells. After 4 h, the monolayers are washed with phosphate-buffered saline and refed media (90% 1:1 Dulbecco's modified essential media (DMEM):F-12+10% fetal bovine serum). The cells are harvested 48-72 h after addition of the DNA by scraping in HME buffer (in mM: 20 HEPES, 5 $MgCl_2$, 1 EDTA, pH 7.4) containing 10% sucrose on ice, and disrupted using a Dounce homogenizer. After centrifugation at 800×g, the supernatant is diluted with HME without sucrose and centrifuged at 100,000×g for 1 h. The resulting pellet is rehomogenized and centrifuged a second hour at 100,000×g. This crude membrane pellet is resuspended in HME with sucrose, aliquoted, and snap-frozen by immersion in liquid nitrogen. The membranes are stored at 70° C. Protein concentration is determined spectroscopically by Bradford protein assay.

GTPγS Binding Assay Using S1P Receptor/HEK293 Membrane Preparations

GTPγS binding experiments are performed as described by DS. Im et al., Mol. Pharmacol. 2000; 57:753. Ligand-mediated GTPγS binding to G-proteins is measured in GTP binding buffer (in mM: 50 HEPES, 100 NaCl, 10 $MgCl_2$, pH 7.5) using 25 μg of a membrane preparation from transiently transfected HEK293 cells. Ligand is added to membranes in the presence of 10 μM GDP and 0.1 nM [$^{35}$S]GTPγS (1200 Ci/mmol) and incubated at 30° C. for 30 min. Bound GTPγS is separated from unbound using the Brandel harvester (Gaithersburg, Md.) and counted with a liquid scintillation counter.

B. In Vivo: Blood Lymphocyte Depletion

A compound of formula I or the vehicle is administered orally by gavage to rats. Tail blood for hematological monitoring is obtained on day −1 to give the baseline individual values, and at 2, 6, 24, 48 and 72 hours after application. In this assay, the compounds of formula I deplete peripheral blood lymphocytes when administered at a dose of 0.03 to 3 mg/kg.

The compounds of formula I are therefore useful as sphingosine-1 phosphate (S1P) receptor agonists or antagonists for:

a) treatment and prevention of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation; particularly in the treatment of acute or chronic allo- and xenograft rejection or in the transplantation of insulin producing cells, e.g. pancreatic islet cells;

b) treatment and prevention of autoimmune disease or of inflammatory conditions, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia greata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis.

For the above uses the required dosage will of course vary depending on the mode of administration, the particular condition to be treated and the effect desired. In general, satisfactory results are indicated to be obtained at daily dosages of from about 0.1 to about 100 mg/kg body weight. An indicated daily dosage in the larger mammal, e.g. humans, is in the range of from about 0.5 mg to 2000 mg, conveniently administered, for example, in divided doses up to four times a day or in retard form.

The compounds of formula I may be administered by any appropriate route, e.g. orally, for example in the form of a tablet or capsule, topically or parenterally, for example intravenously. Pharmaceutical compositions comprising a compound of formula I in free form or in pharmaceutically acceptable salt form in association with at least one pharmaceutically acceptable carrier or diluent may be manufactured in conventional manner by mixing with a pharmaceutically acceptable carrier or diluent. Unit dosage forms for oral administration contain, for example, from about 0.1 mg to about 500 mg of active substance.

Compounds of formula I may be administered in free form or in pharmaceutically acceptable salt form, e.g. as indicated above. Such salts may be prepared in conventional manner and exhibit the same order of activity as the free compounds.

The compounds of formula I may be administered as the sole active ingredient or together with other drugs in immunomodulating regimens or other anti-inflammatory agents e.g. for the treatment or prevention of allograft acute or chronic rejection or inflammatory or autoimmune disorders. For example, they may be used in combination with calcineurin inhibitors, e.g. cyclosporin A, cyclosporin G, FK-506, ABT-281, ASM 981; an mTOR inhibitor, e.g. rapamycin, 40-O-(2-hydroxy)ethyl-rapamycin, CCI779, ABT578 or AP23573 etc.; corticosteroids; cyclophosphamide; azathioprene; methotrexate; another S1P receptor agonist, e.g. FTY 720 or an analogue thereof; leflunomide or analogs thereof; mizoribine; mycophenolic acid; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists.

Where a compound of formula I is administered in conjunction with another immunomodulating or anti-inflammatory agent, dosages of the co-administered immunomodulating or anti-inflammatory agent will of course vary depending on the type of co-drug employed, on the condition to be treated and so forth.

The present invention thus provides:
1. A method of treating or preventing organ or tissue transplant rejection, comprising administering to a subject a therapeutically effective amount of a compound of formula I, or a pharmaceutically acceptable salt thereof.
2. A method of treating or preventing an autoimmune disease or inflammatory condition, comprising administering to a subject a therapeutically effective amount of a compound of formula I, or a pharmaceutically acceptable salt thereof.
3. A compound of formula I, or a pharmaceutically acceptable salt thereof, for use as a pharmaceutical.
4. A pharmaceutical composition comprising a compound of formula I, or a pharmaceutically acceptable salt thereof, and a pharmaceutically acceptable diluent or carrier.
5. Use of a compound of formula I, or a pharmaceutically acceptable salt thereof, for the preparation of a medicament, e.g. in a method as disclosed above.
6. A pharmaceutical combination comprising (a) a compound of formula I and (b) a second drug substance, said second drug substance being suitable for the prevention or treatment of a condition described above.
7. A method as defined above comprising co-administration, e.g. concomitantly or in sequence, of (a) a compound of formula I and (b) a second drug substance, said second drug substance being suitable for the prevention or treatment of a condition described above.

The invention claimed is:

1. A compound with the following formula:

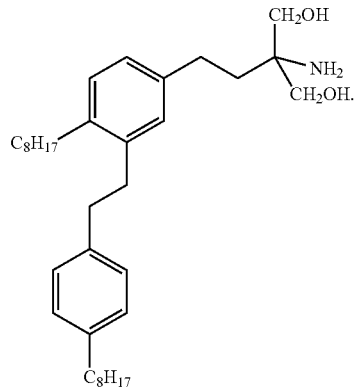

2. A compound with the following formula:

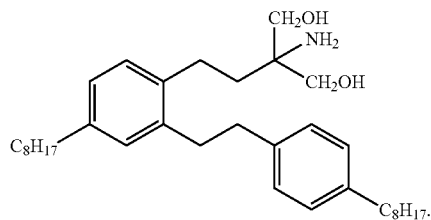

* * * * *